United States Patent [19]
McGeer et al.

[11] Patent Number: 5,532,219
[45] Date of Patent: Jul. 2, 1996

[54] DAPSONE AND PROMIN FOR THE TREATMENT OF DEMENTIA

[75] Inventors: Patrick L. McGeer, Vancouver, Canada; Nobua Harada, Oku-gun; Horoshi Kimura, Otsu, both of Japan; Edith G. McGeer; Michael Schulzer, both of Vancouver, Canada

[73] Assignee: The University of British Columbia, Vancouver, Canada

[21] Appl. No.: 42,658

[22] Filed: Apr. 5, 1993

Related U.S. Application Data

[63] Continuation-in-part of Ser. No. 689,498, Apr. 23, 1991, abandoned.

[51] Int. Cl.$^6$ ........................................... A61K 31/13
[52] U.S. Cl. ................................... 514/42; 514/645
[58] Field of Search ................................. 514/42, 645

[56] References Cited

U.S. PATENT DOCUMENTS

| | | | |
|---|---|---|---|
| 4,791,099 | 12/1988 | Aroonsakul | 514/2 |
| 4,855,308 | 8/1989 | Kester et al. | 514/332 |

FOREIGN PATENT DOCUMENTS

| | | |
|---|---|---|
| 3923088 | 1/1991 | Germany . |

OTHER PUBLICATIONS

"The Merck Index", 1989, Merck & C., Inc., Rahway, N.J., U.S.A., #2820, 4357, 8667, 8664, 8947, 9237.
"The Merck Index", 10th Ed., #2808, 4324 1983.
Capstick et al., 84CA:993111W, 1976.
Stendahl et al., 98CA:1914689, 1983.
P. L. McGeer et al., Dementia, vol. 3, No. 3, 1992 pp. 146–149, "Prevalence of Dementia Amongst Elderly Japanese with Leprosy: Apparent Effect of Chronic Drug Therapy".
Shibayama, H., et al., "Prevalence of Dementia in a Japanese Elderly Population", Actua. Psychiat., Scand. 1986; 74:144–51.
Zuidema, J., et al., "Clinical Pharmacokinetics of Dapsone", Clin. Pharmacokinetics 1986; 11:299–315.
Boesen., P., et al., "Dapsone in Temporal Arteritis and Polymaglia Rheumatica", J. Rheumatol. 1988; 15:879–80.
Lindskov, R. and Reyman F., "Dapsone in the Treatment of Cutaneous Lupus Erythematosus", Dermatologia 1986; 172:214–17.
Sharquie K. E., "Suppression of Behcet's Disease with Dapsone", Brit. J. Dermatol. 1984; 110:493–4.
Guillevin L., "Treatment of Polyarteritis Nodosa with Dapsone", Scand. J. Rheumatol. 1986; 15:95–6.
Gabriel S. E., et al., "Rifampin Therapy in Rheumatol Arthritis", J. Rheumatoid. 1990; 17:163–6.

Van Saane P. and Timmerman H., "Pharmacohistochemical Aspects of Leprosy. Recent Developments and Prospects for New Drugs", Pharm. Weekbl. 1989; 11:3–8 Abstract.
McGeer P. L., et al., "Anti–inflammatory Drugs and Alzhemier's Disease", Lancet 1990; 335:1037.
Evans D. A., et al., "Prevalence of Alzheimer Disease in a Community Population of Older Persons", JAMA 1989; 262:2551–6.
Mortimer J. A., "Alzheimer's Disease and Dementia: Prevalence and Incidence", In: Reisberg B (ed) Alzheimer's Disease, Glencoe, Free Press, 1983.
Sulkava R., et al., "Prevalence of Severe Dementia in Finland", Neurology 1985; 35:1025–9.
Zhang M., et al., "The Prevalence of Dementia and Alzheimer's Disease in Shanghai, China: Impact of Age, Gender and Education", Ann Neurol. 1990: 27:428–37.
Itagaki S., et al., "Presence of T–cytotoxic Suppressor and Leucocyte Common Antigen Positive Cells in Alzheimer's Disease Brain Tissue", Neurosci. Lett. 1988; 91:259–64.
McGeer P. L., et al., "Reactive Microglia in Patients with Senile Dementia of the Alzheimer Type are Positive for the Histocompatibility Glycoprotein, HLA–DR.", Neurosci. Lett. 1987; 79:195–200.
Rogers J., et al., "Expression of Immune System–Associated Antigen by Cells of the Human Central Nervous System. Relationship to the Pathology of Alzheimer's Disease", Neurobiol. Aging 1988; 9:330–49.
McGeer P. L., et al., "Immune System Response in Alzheimer's Disease", Can. J. Neurol. Sci. 1989; 16:516–27.
McGeer P. L., et al., "Activation of hte Classical Complement Pathway in Brain Tissue of Alzheimer Patients", Neurosci. Lett. 1989; 107:341–6.
Akiyama H. and McGeer P. L., "Brain Microglia Constitutively Express β–2 Integrins", J. Neuroimmunol. 1990; 30:81–93.
Eikelenboom P., et al., "Complement Activation in Amyloid Plaques in Alzheimer's Dementia", Virchows Arch. (Cell Pathol.) 1989; 56:259–62.
Cowdry, E. V. and Ruangsivi C., "Influence of Promin, Starch and Heptaldehyde on Experimental Leprosy in Rats", Arch. Pathol. 32:632, 1941.

*Primary Examiner*—Russell Travers
*Attorney, Agent, or Firm*—Oyen Wiggs Green & Mutala

[57] ABSTRACT

This invention pertains to the novel use of 4,4'-diaminodiphenylsulfone and its didextrose sulfonate derivative and other closely related sulfones in the prevention and treatment of dementia (Alzheimer's disease). A method of preventing and treating dementia in a human being suffering from dementia which comprises administering to the human being a therapeutic amount of a substance selected from the group consisting of 4,4'-diaminodiphenylsulfone, its didextrose sulfonate derivative, and sulfoxone, sulfetrone and thiazolsulfone, and therapeutically acceptable salts thereof.

11 Claims, 2 Drawing Sheets

NS = not significant; *p < 0.05; **p < 0.01, chi square test 5,532,219

DAPSONE AND PROMIN FOR THE TREATMENT OF DEMENTIA

This application is a continuation-in-part of application Ser. No. 07/689,498, filed Apr. 23, 1991, now abandoned.

FIELD OF THE INVENTION

This invention pertains to the novel use of 4,4'-diaminodiphenylsulfone and its didextrose sulfonate derivative and closely related anti-lepromatous sulfones in the treatment of dementia (Alzheimer's disease) in human beings.

BACKGROUND OF THE INVENTION

Alzheimer's Disease is by far the most common cause of primary dementia. Either by itself, or in combination with multiple infarcts, it accounts for almost 80% of all cases. No treatment has been established which will prevent the onset or delay the progression of Alzheimer's Disease. It is possible that known drugs would have an as yet unrecognized efficacy in this respect.

4,4'-diaminodiphenylsulfone dapsone and its didextrose sulfonate derivative Promin™ were first shown to have a favourable effect in treating rat leprosy in 1941 (Cowdry and Ruangsiri, Arch. Pathol. 32:632, 1941). Successful clinical trials for the treatment of human leprosy followed and these two compounds are now the most important anti-leprosy drugs. The two drugs have since been used for treating a variety of skin diseases such as dermatitis herpetiformis and efficacy has been reported in several disorders of presumed autoimmune origin such as rheumatoid arthritis, lupus erythematosus and Behcet's disease. Dapsone is a drug that has been used worldwide for over 40 years. It has been found to have few side effects and these are well understood due to extensive experience with patients taking the drug continuously for many years. To the applicants' knowledge, 4,4'-diaminodiphenylsulfone and its didextrose sulfonate derivative, and closely related antilepromatous sulfones have never been used or considered for the treatment of dementia.

Leprosy is no longer a fatal disorder, due in substantial measure to treatment with dapsone. It has anti-inflammatory action, which may seem paradoxical for treatment of an infectious disease. However, *M. leprae* survives in macrophages, and one of the deleterious consequences of the infection, which is reduced by dapsone, is widespread amyloidosis. Dapsone has also been reported to be effective for the treatment of various presumed autoimmune diseases, including dermatitis herpetiformis, rheumatoid arthritis, temporal arteritis, polymyalgia rheumatica, cutaneous lupus erythematosus, Behcet's disease and polyarteritis nodosa. The alternative antileprosy drugs, clofazimine and rifampicin, have also been reported to have efficacy in anti-inflammatory therapeutic applications.

SUMMARY OF THE INVENTION

The invention pertains to a method of treating dementia of the Alzheimer type in a human being suffering from such dementia which comprises administering to the human being a therapeutically effective amount eg. daily to weekly of a substance selected from the group consisting of 4,4'-diaminodiphenylsulfone, glucosulfone (the didextrose sulfonate derivative of 4,4'-diaminodiphenylsulfone), and sulfoxone, sulfetrone, and thiazolsulfone, and therapeutically and pharmaceutically acceptable salts thereof.

The substance can be effectively administered to the human being suffering from dementia at dosage rates which can vary widely, and on schedules which can vary from twice daily to once weekly. The substance can be either 4,4'-diaminodiphenylsulfone, its didextrose sulfonate derivative, other closely related derivatives as mentioned above or pharmaceutically acceptable salts thereof. Typical therapeutic dosages will be in the range of 2 to 20 micromoles per kg body weight per day, and the preferred route will be oral. Typical dosage rate will be between about 50 mg and 300 mg per day.

The invention also pertains to a composition useful for treating dementia comprising substances selected from the group consisting of 4,4'-diaminodiphenylsulfone, the didextrose sulfonate derivative of 4,4'-diaminodiphenylsulfone, sulfoxone, sulfetrone, thiazolsulfone, and pharmaceutically acceptable salts thereof, and a pharmaceutically acceptable carrier.

DRAWINGS

DETAILED DESCRIPTION OF A PREFERRED EMBODIMENT OF THE INVENTION

Figure 1:
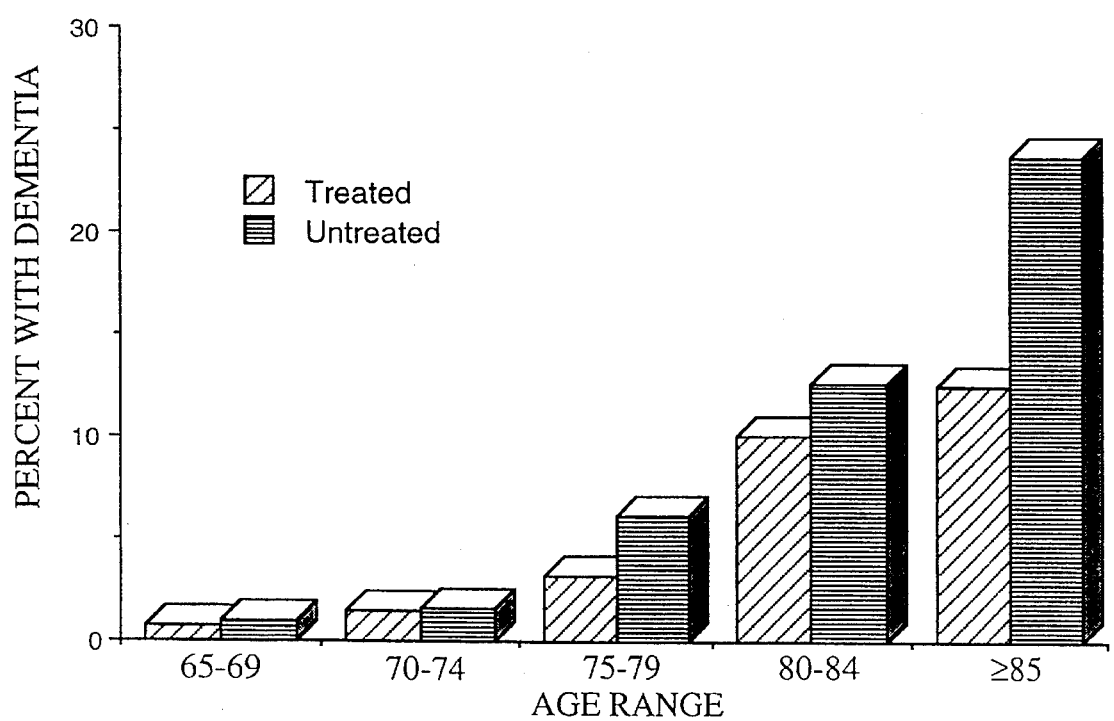
FIG. 1 represents a block graphical comparison of dementia percentage among treated and untreated patients from the age of 65 to over 85.

Immunohistochemical studies on Alzheimer brain tissue have suggested a chronic inflammatory process may play a role in the observed neuronal degeneration. Dapsone, 4,4'-diaminodiphenylsulfone, is effective in several chronic inflammatory disorders.

Leprosy patients are almost universally treated with 4,4-diaminodiphenylsulfone (dapsone), the didextrose sulfonate derivative (Promin™), or other closely related sulfones, over prolonged periods. As a result of such treatment, and the availability of these drugs, leprosy is no longer fatal, and in many cases apparent cures can lead to drug withdrawal. The applicants have noted unexpectedly that the prevalence of dementia (Alzheimer disease) amongst elderly leprosy patients being treated with either of the two drugs noted has been unusually low.

The applicants have conducted a formal survey of leprosy hospitals in Japan and have determined that there was significantly less prevalence of dementia amongst dapsone and Promin™ treated leprosy patients compared with those who had been off such drugs for at least five years. It has therefore been concluded that dapsone and Promin™, when administered on a daily dosage basis to the elderly patient, have a preventative action against dementia.

One of the inventors observed that on the Japanese island of Nagashima, leprosy patients seemed to have a low prevalence of dementia. Patients on this island live independently, but are under close medical supervision.

In a survey of thirteen national and three private leprosy hospitals in Japan, the prevalence of dementia in patients 65 years and over was determined according to whether they were still receiving continuous treatment with 4,4'-diaminodiphenylsulfone, its didextrose sulfonate derivative or other related anti-leprosy drugs, had received intermittent treatment, or no drug treatment with such chemicals over the previous five years.

The overall prevalence of dementia was 2.9% of the continuously treated 1,410 patients 65 years and over. This compares with 4.83% of 621 intermittently treated cases and 6.25% of 1,761 cases untreated for at least five years. Multiple logistic regression analysis showed a highly significant increase of dementia with age (p=0.0001) and, after age adjustment, a significant reduction of dementia in patients on continuous drug treatment as compared with patients free of drugs for at least five years (p=0.017). Treatment had no significant effect on the prevalence of strokes. The dementia figure for untreated cases was virtually double and compared closely with the figure of 6.25% reported by Shibayami et al. for the Japanese population over 65 years of age (Acta. Psychiat. Scand. 74:144–151, 1986). Statistical analysis of these data show that the probability of developing dementia is reduced to 63% by treatment with either dapsone or Promin™. These data show preliminary evidence of the effectiveness of dapsone and Promin™ in retarding the development of dementia.

Methods

Each institute was asked to categorize their elderly (65 years of age or over) patients according to age range and drug treatment over the past five years (continuously on dapsone, Promin™ or other anti-lepromatous drug; free of drug treatment; or on intermittent treatment). In each category, the total number of patients and the numbers with dementia or stroke were to be enumerated. In this survey, no attempt was made to identify the nature of the dementia except that persons who had had a clearly identified stroke in the absence of previous dementia were to be classed in the stroke, rather than the demented groups. In the treatment group overall, 1,240 (88%) had been treated with dapsone, 53 (3.76%) with Promin™, which is the didextrose sulfonate derivative of dapsone, and the rest with other antileprosy drugs. The percentages of demented were highly similar in these subgroups so that they were combined for analysis. The statistical analysis of the data was complicated by the sharp dependence of dementia on age and the failure of the groups to be precisely age-matched. Accordingly, the data on the treated and untreated groups were subjected to logistic regression analysis to determine their level of significance.

Results

The results for the treated, untreated and intermittently treated groups are summarized in Table 1:

The overall prevalence of dementia was 2.9% of the 1,410 continuously treated cases, 4.83% of the 621 intermittently treated cases, and 6.25% of the 1,761 cases untreated for at least five years. For stroke, the comparative figures were 2.27%, 2.90% and 3.24% respectively.

Statistical analysis showed that:

(a) There is a significant increase of dementia with age (p=0.0001), with a logistic regression coefficient of 0.1721, but there is no age-by-treatment interaction (p=0.60). This means that aging has the same effect on the prevalence of dementia in both groups and that the odds of developing dementia in either group increase at an annual rate of 18.8%.

(b) After adjustment for age, the effect of treatment is significant (p=0.017), with a logistic regression coefficient of −0.4633. This means that the odds of developing dementia at any age are reduced by drug treatment to 63% of the corresponding odds in the untreated group (FIG. 1.).

(c) After adjusting for age by logistic regression, treatment had no significant effect on the prevalence of strokes (p=0.30); age, however, was highly significant (p=0.0002), with a logistic regression coefficient of 0.0609, meaning that the odds of developing a stroke in either group increase at an annual rate of 6%.

The reason for hypothesizing that anti-inflammatory therapy might be effective in preventing or slowing down the progression of Alzheimer's Disease is the accumulation of evidence suggesting that a chronic inflammatory state of the brain exists in this disease. Reactive microglia, which are rarely seen in normal brain tissue, are abundant in Alzheimer's Disease brain tissue. They strongly express class II major histocompatibility complex (MHC) glycoproteins, Fc receptors, and various $\beta 2$ integrins which are complement receptors. There are also significant numbers of T cells in the tissue matrix. Brain tissue in affected areas is strongly stained by antibodies to a number of complement proteins, including C1q, C3d, C4d and the membrane attack complex C5b-9. This latter finding suggests that some of the neuronal degeneration in Alzheimer's Disease may be due to bystander lysis.

Therapeutic Dosage

Dapsone, Promin™, sulfoxone, sulfetrone and thiazolsulfone are all preferentially administered in oral tablet or enteric coated capsule form. Parenteral administration is possible, since some derivatives, such as Promin™, are highly soluble in water, and can be prepared in ampules as an aqueous solution of up to 40% concentration. The dosages of sulfones and methods of administration for the

TABLE 1

| AGE RANGE | CASES TREATED FOR 5 YEARS | | | | | CASES NOT TREATED FOR 5 YEARS | | | | | INTERMITTENTLY TREATED CASES | | | | |
|---|---|---|---|---|---|---|---|---|---|---|---|---|---|---|---|
| | Total | Demented | | With Strokes | | Total | Demented | | With Strokes | | Total | Demented | | With Strokes | |
| | No. | No. | % | No. | % | No. | No. | % | No. | % | No. | No. | % | No. | % |
| 65–69 | 529 | 4 | 0.76 | 7 | 1.32 | 489 | 5 | 1.02 | 11 | 2.25 | 211 | 1 | 0.47 | 7 | 3.31 |
| 70–74 | 410 | 6 | 1.46 | 10 | 2.44 | 445 | 7 | 1.57 | 9 | 2.02 | 176 | 3 | 1.70 | 3 | 3.31 |
| 75–79 | 257 | 8 | 3.11 | 7 | 2.72 | 376 | 23 | 6.10 | 13 | 3.46 | 122 | 4 | 3.28 | 2 | 1.64 |
| 80–84 | 150 | 15 | 10.0 | 5 | 3.33 | 286 | 36 | 12.55 | 13 | 4.55 | 69 | 8 | 11.59 | 4 | 5.80 |
| ≧85 | 64 | 8 | 12.5 | 3 | 4.67 | 165 | 39 | 23.60 | 11 | 6.67 | 43 | 14 | 32.56 | 2 | 4.65 |
| OVERALL | | | | | | | | | | | | | | | |
| ≧65 | 1410 | 41 | 2.9 | 32 | 2.27 | 1761 | 110 | 6.25 | 57 | 3.24 | 621 | 30 | 4.83 | 18 | 2.90 | retardation of dementia will be comparable to those now used for the treatment of leprosy and dermatitis herpetiformis. Typical dosages of dapsone will vary from 100–200 mg once daily, to 200–400 mg twice weekly, to 300–600 mg once weekly. Tablets can be of any convenient size, but typically will be of 100 mg. Promin™ and the other sulfones specified will be administered in equivalent molecular doses. As in leprosy, the drugs will be continued indefinitely. Lifetime treatment following clinical diagnosis of probable dementia of the Alzheimer type is anticipated.

EXAMPLE I

Neurofibrillary Tangles and Senile Plaques in Brain of Elderly Leprosy Patients

Yoshio Namba et al. of the Department of Ultrastructure and Histochemistry, Tokyo Institute of Psychiatry, have examined necropsy brains for the occurrence of neurofibrillary tangles (NFT's) and senile plaques (SP's), which are the neuropathological hallmarks of SDAT.

Namba et al. examined 16 brains from leprosy patients (aged up to 70 years) without dementia from the National Institute for Leprosy Research, Tokyo, Japan. They immunostained the sections of each temporal lobe, including the hippocampus, parahippocampal gyrus, and occipitotemporal gyrus, with rabbit antibody to tau protein (provided by Dr. Y. Ihara) to demonstrate NFT's, and mouse monoclonal antibody to β protein (provided by Dr. D. Allsop) for SP's. The number of NFT's and SP's were counted semiquantitatively in a low-power field. For comparison, they used standard immunohistochemical data of the frequency of NFT's and SP's in 140 Japanese non-demented elderly subjects (aged up to 70 years).

Figure 2:
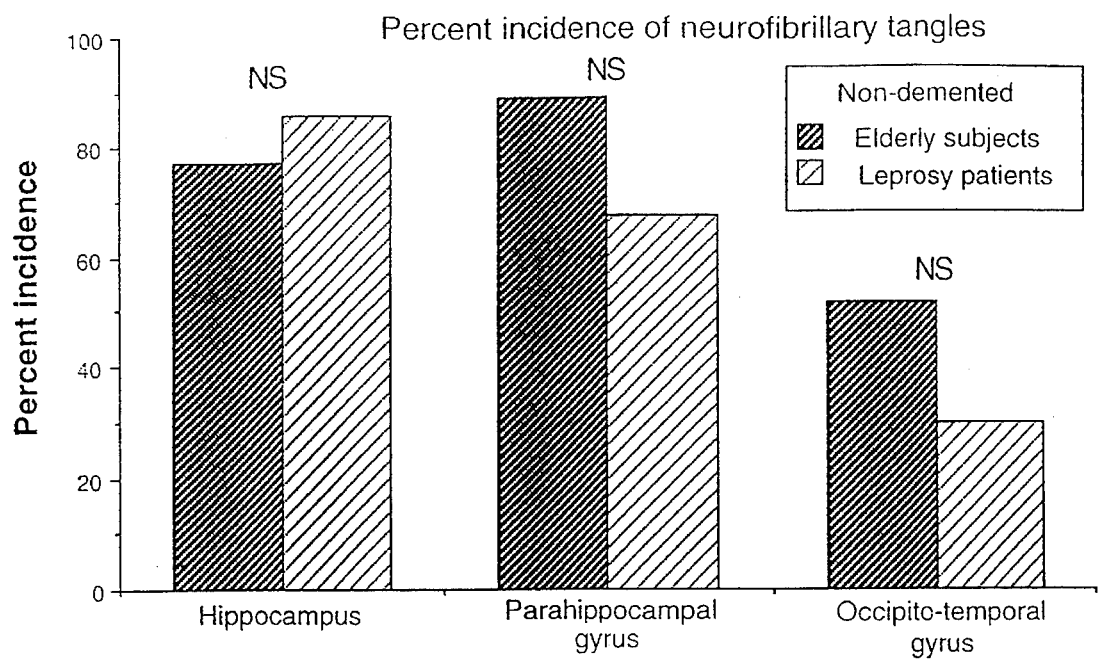
FIGS. 2 and 3 represent block graphical comparisons of frequency of NFT's and SP's among leprosy and non-leprosy subjects aged over 70 years.
Figure 3:
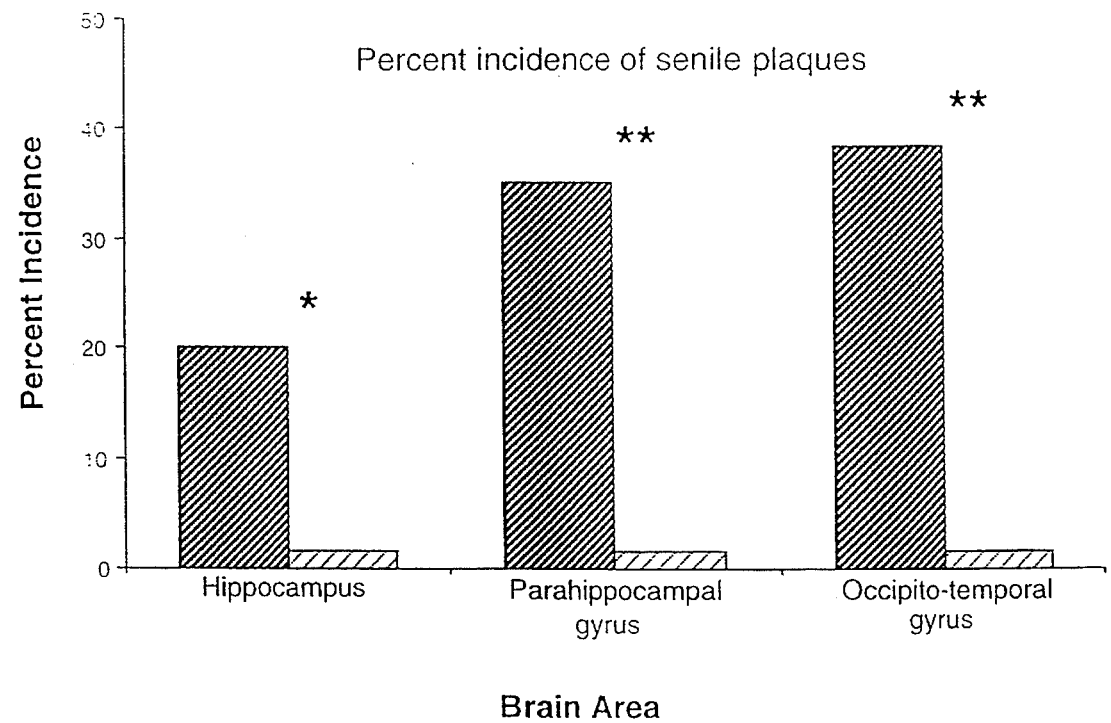

Namba et al. found NFT's in varying amounts in hippocampus, parahippocampal gyrus, and occipitotemporal gyrus in leprosy patients. There was no significant difference in the frequency between their data and the standard data (see FIGS. 2 and 3). By contrast, they found no SP's in the leprosy patients ($p<0.05$ or $p<0.01$ for each of the three brain regions). The lack of SP's was ocnfirmed by the examination of sections stained with Bilshowsky's silver impregnation.

The absence of SP's in the hippocampal, parahippocampal, and occipitotemporal regions in elderly, non-demented leprosy patients was surprising, in view of the similar occurrence of NFT's in the two groups of elderly subjects. *Mycobacterium leprae* infection and/or continuous or intermittent use of anti-inflammatory drugs may be relevant. Although the lack of SP's itself is not necessarily correlated with the supposed low prevalence of dementia in leprosy patients, their results may help in the clarification of the pathogenesis of SP's.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

REFERENCES

Shibayama H., Kasahara Y., Kobayashi H. Prevalence of dementia in a Japanese elderly population. Actua. Psychiat. Scand. 1986; 74: 144–51.

Zuidema J., Hilbera-Modderman E. S. M., Merkus F. W. H. M. Clinical pharmacokinetics of dapsone. Clin. Pharmacokinetics 1986; 11:299–315.

Boesen P., Dideriksen K., Stentoft J., Jensen M. K. Dapsone in temporal arteritis and polymaglia rheumatica. J. Rheumatol. 1988; 15:879–80.

Lindskov R., Reymann F. Dapsone in the treatment of cutaneous lupus erythematosus. Dermatologia 1986; 172:214–17.

Sharquie K. E. Suppression of Behcet's disease with dapsone. Brit. J. Dermatol. 1984; 110:493–4.

Guillebin L. Treatment of polyarteritis nodosa with dapsone. Scand. J. Rheumatol. 1986; 15:95–6.

Gabriel S. E., Conn D. L., Luthra H. Rifampin therapy in rheumatoid arthritis. J. Rheumatol. 1990; 17:163–6.

Van Saane P., Timmerman H. Pharmacohistochemical aspects of leprosy. Recent developments and prospects for new drugs. Pharm. Weekbl. 1989; 11:3–8.

McGeer P. L., McGeer E. G., Rogers J., Sibley J. Anti-inflammatory drugs and Alzheimer's disease. Lancet 1990; 335:1037.

Evans D. A., Funkenstein H. H., albert M. S. et al. Prevalence of Alzheimer disease in a community population of older persons. JAMA 1989; 262:2551–6.

Mortimer, J. A. Alzheimers' disease and dementia: prevalence and incidence. In: Reisberg B (ed) Alzheimer's Disease, Glencoe, Free Press, 1983.

Sulkava R., Wikstrom J., Aromaa A. et al. Prevalence of severe dementia in Finland. Neurology 1985; 35:1025–9.

Zhang M., Katzman R., Salmon D. et al. The prevalence of dementia and Alzheimer's disease in Shanghai, China: impact of age, gender and education. Ann Neurol. 1990; 27:428–37.

Itagaki S., McGeer P. L., Akiyama H. Presence of T-cytotoxic suppressor and leucocyte common antigen positive cells in Alzheimer's disease brain tissue. Neurosci. Lett. 1988; 91:259–64.

McGeer P. L., Itagaki S., Tago H., McGeer E. G. Reactive microglia in patients with senile dementia of the Alzheimer type are positive for the histocompatibility glycoprotein, HLA-DR. Neurosci. Lett. 1987; 79:195–200.

Rogers J., Luber-Narod J., Styren S. d., Civin W. H. Expression of immune system-associated antigen by cells of the human central nervous system. Relationship to the pathology of Alzheimer's disease. Neurobiol. Aging 1988; 9:330–49.

McGeer P. L., Akiyama H., Itagaki S., McGeer E. G. Immune system response in Alzheimer's disease. Can. J. Neurol. Sci. 1989; 16:516–27.

McGeer, P. L., Akiyama H., Itagaki S., McGeer E. G. Activation of the classical complement pathway in brain tissue of Alzheimer patients. Neurosci. Lett. 1989; 107:341–6.

Akiyama H., McGeer P. L. Brain microglia constitutively express β-2 integrins. J. Neurolimmunol. 1990; 30:81–93.

Eikelenboom P., Hack. C. E., Rozemuller J. M., Stam F. C. Complement activation in amyloid plaques in Alzheimer's dementia. Virchows Arch. (Cell Pathol.) 1989; 56:259–62.

What is claimed is:

1. A method of treating Alzheimer's disease in a patient, in need of such treatment, which comprises:

administering to the human being a therapeutically effective amount of a substance selected from the group consisting of 4,4'-diaminodiphenylsulfone, the didextrose sulfonate derivative of 4,4'diaminodiphenylsulfone (glucosulfone), sulfoxone, sulfetrone and thiazolsulfone, and therapeutically and pharmaceutically acceptable salts thereof;

the human having no clinical symptoms of leprosy, dermatitis herpetiformis, temporal arteritis, giant cell arteritis, rheumatoid arthritis, Behcet's disease, polymyalgia rheumatica, polychondritis or cutaneous lupus erythematosus.

2. A method as claimed in claim 1 wherein when the substance is 4,4'-diaminodiphenylsulfone it is administered to the human being at a dosage rate of between about 50 mg and 300 mg per day, or when it is glucosulfone, sulfoxone, sulfetrone or thiazolsulfone, it is administered at its equivalent in molecular concentration.

3. A method as claimed in claim 1 wherein the substance is 4,4'-diaminodiphenylsulfone.

4. A method as claimed in claim 1 wherein the substance is the didextrose sulfonate derivative of 4,4'-diaminodiphenylsulfone.

5. A method as claimed in claim 1 wherein the substance is sulfoxone, sulfetrone or thiazolsulfone.

6. A method as claimed in claim 1 wherein the dosage rate is between about 50 mg and 300 mg per day.

7. A method of treating dementia of the Alzheimer type, in a human being exhibiting symptoms of Alzheimer type dementia, comprising:

administering to the human being 4,4'-diaminodiphenylsulfone at a dosage rate of between about 50 mg and 300 mg per day;

the human being having no clinical symptoms of leprosy, dermatitis herpetiformis, temporal arteritis, giant cell arteritis, rheumatoid arthritis, Behcet's disease, polymyalgia rheumatica, polychondritis or cutaneous lupus erythematosus.

8. A method of treating the development of dementia of the Alzheimer type, in a human being diagnosed as susceptible to the development of Alzheimer type dementia, which comprises:

administering to the human being a therapeutically effective amount of a substance selected from the group consisting of 4,4'-diaminodiphenylsulfone, the didextrose sulfonate derivative of 4,4'diaminodiphenylsulfone (glucosulfone), sulfoxone, sulfetrone and thiazolsulfone, and therapeutically and pharmaceutically acceptable salts thereof;

the human being having no clinical symptoms of leprosy, dermatitis herpetiformis, temporal arteritis, giant cell arteritis, rheumatoid arthritis, Behcet's disease, polymyalgia rheumatica, polychondritis or cutaneous lupus erythematosus.

9. The method as claimed in claim 8, wherein the substance is 4,4'diaminodiphenylsulfone and the dosage rate is between about 50 mg and 300 mg per day.

10. A method of treating Alzheimer's disease in a patient, in need of such treatment, which comprises:

administering to the human being a therapeutically effective amount of a substance selected from the group consisting of 4,4'-diaminodiphenylsulfone, the didextrose sulfonate derivative of 4,4'diaminodiphenylsulfone (glucosulfone), sulfoxone, sulfetrone and thiazolsulfone, and therapeutically and pharmaceutically acceptable salts thereof;

the human being having no clinical symptoms of disease.

11. The method as claimed in claim 10, wherein the substance is 4,4'diaminodiphenylsulfone and the dosage rate is between about 50 mg and 300 mg per day.

* * * * *